(12) United States Patent
Moulton et al.

(10) Patent No.: US 11,744,506 B2
(45) Date of Patent: Sep. 5, 2023

(54) SYSTEMS AND METHODS FOR ANALYZING CONCUSSION BIOMARKERS

(71) Applicant: THE CHILDREN'S MEDICAL CENTER CORPORATION, Boston, MA (US)

(72) Inventors: Eric A. Moulton, Boston Charlestown, MA (US); David Borsook, Concord, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 309 days.

(21) Appl. No.: 17/018,286

(22) Filed: Sep. 11, 2020

(65) Prior Publication Data
US 2021/0077008 A1    Mar. 18, 2021

Related U.S. Application Data

(60) Provisional application No. 62/899,580, filed on Sep. 12, 2019.

(51) Int. Cl.
*A61B 5/00* (2006.01)
*A61B 3/107* (2006.01)
(Continued)

(52) U.S. Cl.
CPC .......... *A61B 5/4076* (2013.01); *A61B 3/107* (2013.01); *A61B 3/14* (2013.01); *A61B 5/4041* (2013.01); *A61B 5/4893* (2013.01); *A61B 5/7264* (2013.01); *A61B 5/746* (2013.01); *G06T 7/0014* (2013.01); *G06T 2207/10056* (2013.01);
(Continued)

(58) Field of Classification Search
CPC ....... A61B 5/4041; A61B 5/7264; A61B 3/14; A61B 5/4893; A61B 3/107; A61B 5/746; A61B 5/4076; A61B 3/0025; G06T 7/0012; G06T 7/0014; G06T 2207/30204;
(Continued)

(56) References Cited

U.S. PATENT DOCUMENTS

2004/0096089 A1    5/2004    Borsook et al.
2008/0039737 A1    2/2008    Breiter et al.
(Continued)

OTHER PUBLICATIONS

Binder, "Persisting symptoms after mild head injury: A review of the postconcussive syndrome." Journal of clinical and experimental neuropsychology 8.4 : 323-346 (1986).
(Continued)

*Primary Examiner* — Ishrat I Sherali
(74) *Attorney, Agent, or Firm* — NIXON PEABODY LLP

(57) ABSTRACT

The various examples of the present disclosure are directed towards systems and methods for diagnosing brain health. An exemplary system includes a microscope, a processor, and a memory. The microscope outputs image data of a cornea of a patient. The memory has a plurality of stored code sections, which, when executed by the processor, include instructions for analyzing cornea image data to determine brain health. The instructions begin with receiving cornea image data from the microscope. The instructions then provide for determining at least one marker from the received cornea image data. The instructions then provide for outputting a brain health diagnosis based on the at least one marker.

20 Claims, 10 Drawing Sheets

(51) Int. Cl.
*A61B 3/14* (2006.01)
*G06T 7/00* (2017.01)
(52) U.S. Cl.
CPC ............... *G06T 2207/20081* (2013.01); *G06T 2207/30041* (2013.01); *G06T 2207/30204* (2013.01)
(58) Field of Classification Search
CPC . G06T 2207/30016; G06T 2207/30041; G06T 2207/20081; G06T 2207/10056
USPC ........................................................ 382/128
See application file for complete search history.

(56) References Cited

U.S. PATENT DOCUMENTS

| | | | | |
|---|---|---|---|---|
| 2014/0270052 | A1* | 9/2014 | Vestevich | A61B 6/482 378/4 |
| 2016/0015289 | A1* | 1/2016 | Simon | A61B 5/14552 600/301 |
| 2016/0192873 | A1* | 7/2016 | Kelly | A61B 5/00 351/209 |
| 2017/0124699 | A1* | 5/2017 | Lane | G06V 40/19 |
| 2019/0200862 | A1* | 7/2019 | Krueger | A61B 3/112 |

OTHER PUBLICATIONS

Cavalcanti et al. "In vivo confocal microscopy detects bilateral changes of corneal immune cells and nerves in unilateral herpes zoster ophthalmicus." The ocular surface 16.1: 101-111 (2018).
Chew et al. "Pharmacological management of neurobehavioral disorders following traumatic brain injury—a state-of-the-art review." Journal of rehabilitation research & development 46.6: 851-879 (2009).
Cruzat et al., "In vivo confocal microscopy of corneal nerves in health and disease." The ocular surface 15.1: 15-47 (2017).
Culver et al. "Cibinetide improves corneal nerve fiber abundance in patients with sarcoidosis-associated small nerve fiber loss and neuropathic pain." Investigative ophthalmology & visual science 58.6: BIO52-BIO60 (2017).
Hertz et al. "Reproducibility of in vivo corneal confocal microscopy as a novel screening test for early diabetic sensorimotor polyneuropathy." Diabetic Medicine 28.10: 1253-1260 (2011).
Lewandowski et al. "Measuring post-concussion symptoms in adolescents: feasibility of ecological momentary assessment." Archives of clinical neuropsychology 24.8: 791-796 (2009).
McKee et al. "Military-related traumatic brain injury and neurodegeneration." Alzheimer's & Dementia 10: S242-S253 (2014).
Meaney et al. "Biomechanics of concussion." Clinics in sports medicine 30.1: 19-vii (2011).
Meehan. "Medical therapies for concussion." Clinics in sports medicine 30.1: 115-ix (2011).
Mittenberg et al. "Treatment of post-concussion syndrome following mild head injury." Journal of clinical and experimental neuropsychology 23.6: 829-836 (2001).
Müller et al. "Corneal nerves: structure, contents and function." Experimental eye research 76.5: 521-542 (2003).
Noseda et al., "Migraine pathophysiology: anatomy of the trigeminovascular pathway and associated neurological symptoms, cortical spreading depression, sensitization, and modulation of pain." Pain 154: S44-S53 (2013).
Reddy et al. "A treatment paradigm for sports concussion." Brain Injury Professional 4:24-25 (2004).
Samantaray et al. "Therapeutic potential of melatonin in traumatic central nervous system injury." Journal of pineal research 47.2: 134-142 (2009).
Tavakoli et al. "Normative values for corneal nerve morphology assessed using corneal confocal microscopy: a multinational normative data set." Diabetes Care 38.5: 838-843 (2015).
Tenovuo, "Pharmacological enhancement of cognitive and behavioral deficits after traumatic brain injury." Current opinion in neurology 19.6: 528-533 (2006).
Toledo et al. "The young brain and concussion: imaging as a biomarker for diagnosis and prognosis." Neuroscience and biobehavioral reviews 36.6: 1510-1531 (2012).
Wang et al., "In vivo confocal microscopy of the human cornea in the assessment of peripheral neuropathy and systemic diseases." BioMed research international (2015): Article 951081.
Warden et al. "Guidelines for the pharmacologic treatment of neurobehavioral sequelae of traumatic brain injury." Journal of neurotrauma 23.10: 1468-1501 (2006).

* cited by examiner

610

620

630

640

Healthy Control mTBI

Patient 1　　　　　Patient 2　　　　　Patient 3

SYSTEMS AND METHODS FOR ANALYZING CONCUSSION BIOMARKERS

CROSS-REFERENCE TO RELATED APPLICATIONS

This application is a 35 U.S.C. § 111(a) Utility application which claims benefit under 35 U.S.C. § 119(e) of U.S. Provisional Application No. 62/899,580 filed Sep. 12, 2019, the contents of which is incorporated herein by reference in its entirety.

FIELD

The present disclosure relates to systems and methods for identifying and analyzing concussion biomarkers.

BACKGROUND

Concussions are notoriously difficult to accurately diagnose by conventional systems and methods. Conventional methods rely on drawing blood, performing memory tests on the patient, and tracking eye movement of the patient. In many cases, these tests require subjective judgments by a health care professional and subjective judgments by the patient. For example, conventional questions ask the patient if he feels sluggish, if he has concentration or memory problems, if he has confusion, if he has double vision, and other similar questions. These questions identify that the patient might be experiencing trauma but do not clearly indicate that the trauma stems from concussion. Furthermore, more objective measures, like blood tests or computed tomography (CT) scans, require extra equipment, costs, and time and often have low accuracy ratings as well. The inability to accurately diagnose a concussion has long-term implications on whether the patient is treated properly.

Furthermore, conventional methods also fail to quickly and accurately evaluate patient treatment. Often, health professionals must rely either on expensive, time-intensive methods like CT or magnetic resonance imaging (MRI) brain scans or a patient's subjective account of their performance. Therefore, there is deficiency in evaluating whether a concussion patient is successfully recovering.

SUMMARY

The various examples of the present disclosure are directed towards a system for diagnosing brain health. The system includes a microscope, a processor, and a memory. The microscope outputs image data of a cornea of a patient. The memory has a plurality of stored code sections, which, when executed by the processor, include instructions for analyzing cornea image data to determine brain health. The instructions begin with receiving cornea image data from the microscope. The instructions then provide for determining at least one marker from the received cornea image data. The instructions then provide for outputting a brain health diagnosis based on the at least one marker.

In some examples, each of the at least one marker includes a cornea nerve fiber characteristic. For example, the cornea nerve fiber characteristic includes at least one of: a nerve fiber density, a nerve branch density, a nerve fiber length, a nerve fiber total branch density, a nerve fiber area, a nerve fiber width, a nerve fiber orientation histogram, and a nerve fiber width histogram.

In some examples, receiving cornea image data includes receiving a first set of cornea image data and receiving a second set of cornea image data. For example, the brain health diagnosis is based on determining a difference between the at least one marker in the first set of cornea image data and the at least one marker in the second set of cornea image data.

In some examples, the first set of cornea image data corresponds to a left eye of a patient and the second set of cornea image data corresponds to a right eye of a patient. In some examples, the first set of cornea image data corresponds to image data with at a first time, and the second set of cornea image data corresponds to image data at a second time. For example, the first time is earlier than the second time.

In some examples, the brain health diagnosis includes at least one of a concussion severity notification and a notification identifying whether a concussion has occurred.

In some examples, determining the at least one marker from the received cornea image data includes (1) identifying a plurality of markers in the received cornea image data and (2) selecting, via a machine learning algorithm, one or more of the identified markers.

In some examples, the machine learning model is trained on a plurality of sets of cornea image data. For example, the sets of cornea image data include at least one set of cornea image data corresponding to a healthy subject and at least one set of cornea image data corresponding to a subject with a concussion.

In a second embodiment, the present disclosure provides for a method for diagnosing brain health. The method provides for first receiving cornea image from a microscope. The method then provides for determining at least one marker from the received cornea image data. The method then provides for outputting a brain health diagnosis based on the at least one marker. Additional examples of the second embodiment are as provided for above with respect to the first embodiment.

In a third embodiment, the present disclosure provides for a non-transitory machine-readable medium comprising machine-executable code. When executed by at least one machine, the machine-executable code causes the machine to (1) receive cornea image data from a microscope, (2) determine at least one marker from the received cornea image data, and (3) output a brain health diagnosis based on the at least one marker. Additional examples of the third embodiment are as provided for above with respect to the first embodiment.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Figure 1:
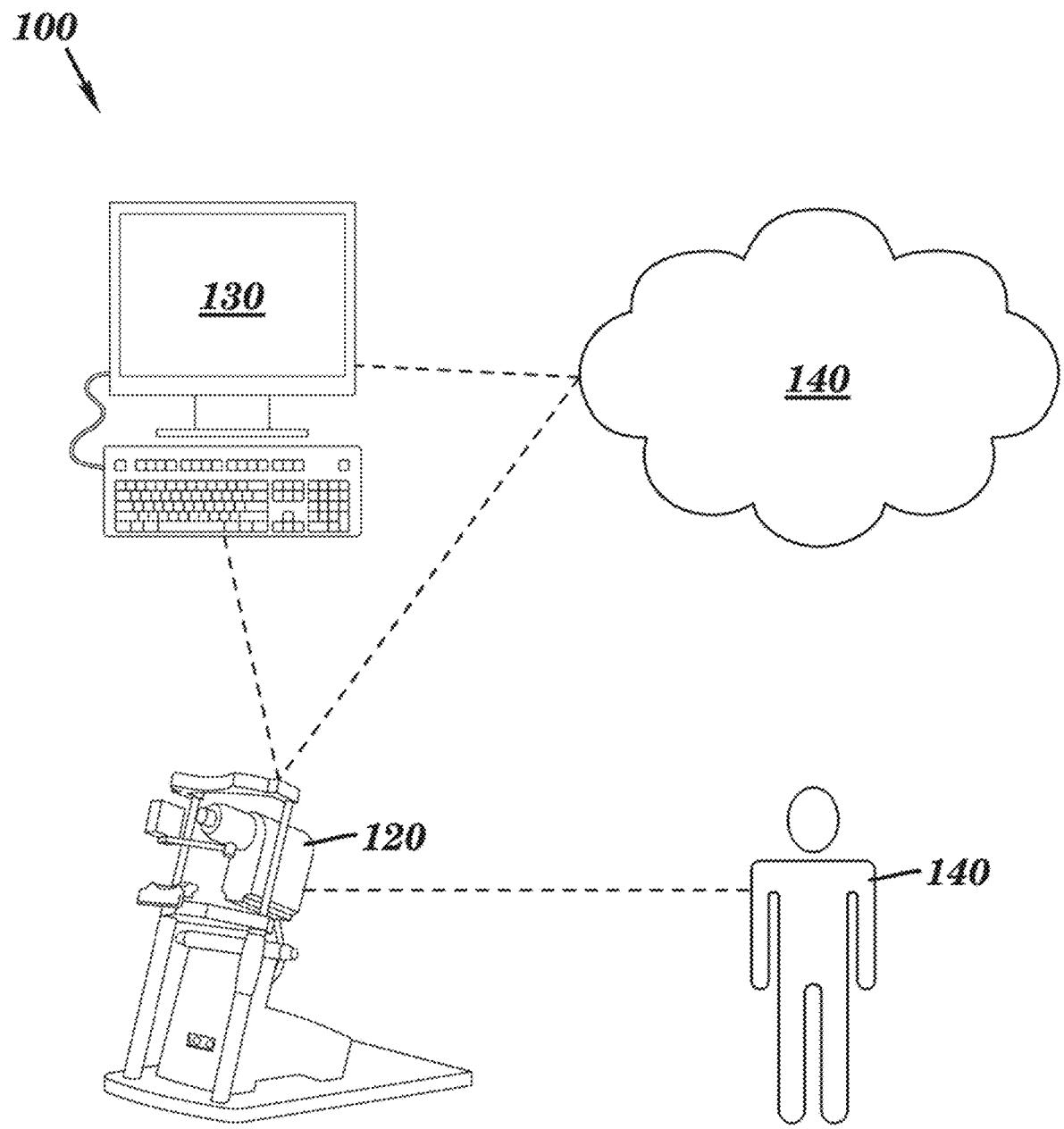
FIG. 1 shows an exemplary system for evaluating concussion biomarkers, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure is directed to an image test, which quickly, non-invasively, and accurately diagnoses (1) whether a concussion has occurred and (2) the severity of said concussion. The present disclosure provides for first receiving cornea image data from a microscope, determining at least one marker from the received image data, and then outputting a brain health diagnosis based on the marker. In some examples of the present disclosure, the present disclosure provides for looking for a change in the cornea biomarkers over time to evaluate treatment, repeat concussions, or general brain health of a subject.

FIG. 1 shows an exemplary system 100 for evaluating concussion biomarkers, according to an embodiment of the present disclosure. System 100 provides for a subject 110, a microscope 120, a computing device 130, and a network 140.

The microscope 120 receives eye image data from the subject 110. For example, the microscope 120 is configured to receive image data corresponding to a cornea of the patient. Human corneas have high nerve densities, and can be viewed with a conventional microscope. As discussed further below with respect to FIGS. 2-3, the present disclosure provides for examining cornea nerve health to identify concussions and determine general brain health. In some examples, the microscope 120 is configured to receive image data of one or both eyes of subject 110. In some examples, the microscope 120 is any of a retinal camera, an ophthalmoscope, a manual keratometer, a slit lamp, and any other measuring device configured to capture image data of a patient's cornea. In some examples, the microscope 120 is configured to output photographic or video image data of the cornea of the subject 110. In some examples, the microscope is a laser scanning in vivo confocal microscope, including for instance, a Heidelberg Retinal Tomograph I/III with a Rostock Corneal Module.

The computing device 130 receives the cornea image data output by the microscope 120. For example, the computing device 130 includes a memory module, a processor, and a communication element. In some examples, the communication element is configured to receive wired or wireless transmissions from the network 140 or the microscope 120. In some examples, the computing device 130 receives the cornea image data by a user's manual entry of the data (e.g., the patient 110 or a health professional assisting the patient 110). In other examples, the microscope 120 is configured to automatically transmit the image data directly to the computing device 130, or to the computing device 130 via the network 140. In some examples, the computing device 130 is configured to receive cornea image data or other health data from other external computing devices (not pictured) through the network 140.

Therefore, unlike conventional systems and methods, system 100 provides a quick evaluation system which can determine concussion status locally with the patient. Such a system is low cost, transportable, and does not require sending data to an external lab and waiting for external processing of the data.

Figure 2:
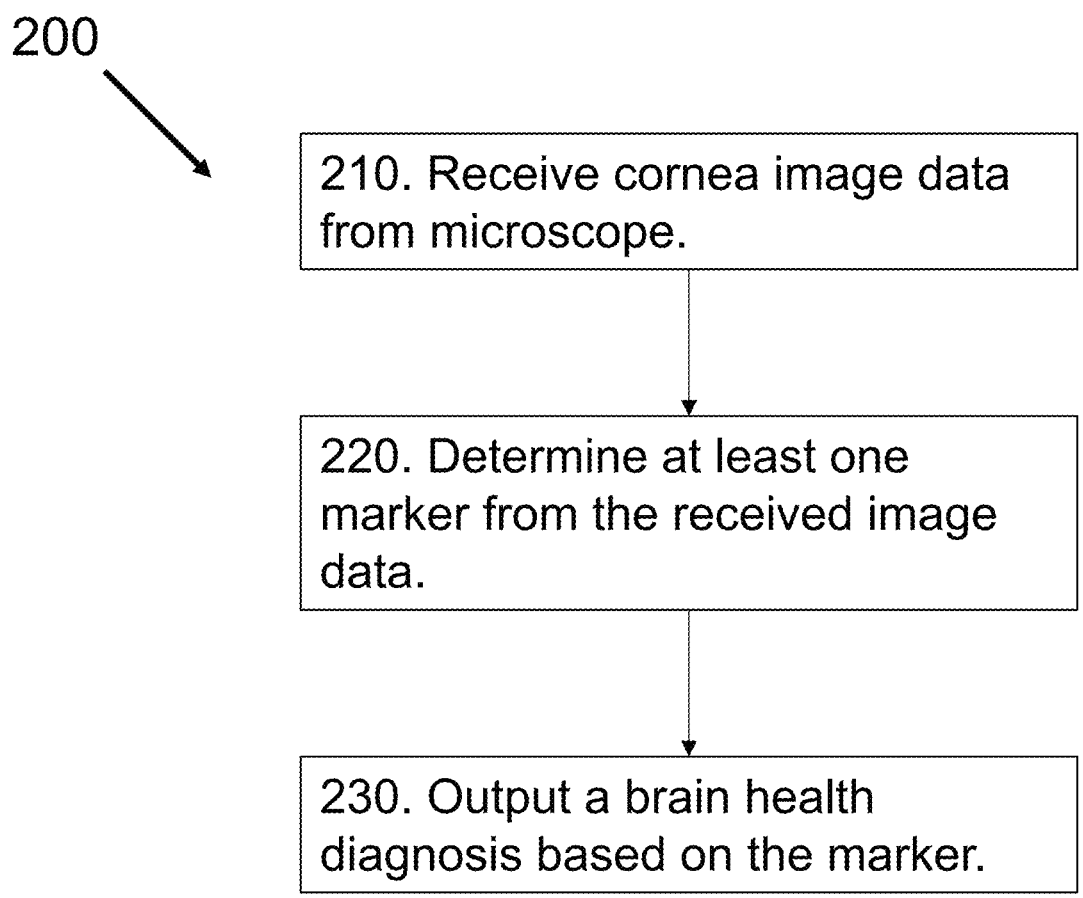
FIG. 2 shows an exemplary method for evaluating concussion biomarkers, according to an embodiment of the present disclosure.

FIG. 2 shows an exemplary method 200 for evaluating concussion biomarkers, according to an embodiment of the present disclosure. In some examples, method 200 is performed on system 100, as discussed above with respect to FIG. 1.

Method 200 begins by receiving cornea image data from a microscope 210. For example, the cornea image data is received by the computing device 130 from the microscope 120 of FIG. 1. In some examples, a set of image data, which includes image data (e.g., photographic) of a subject's cornea at various depth levels, is received. In some examples, additional cornea image data is received from an external computing device or from manual entry by a health professional.

In some examples, more than one set of image data is received. For example, a first set of image data is received from a first time period, and a second set of image data is received from a second time period, subsequent to the first time period. For example, a health professional collects regular cornea image data from a subject to evaluate brain health over time. In some examples, the first and second set of cornea image data correspond, respectively, to a right and left eye of a subject.

In some examples, the received cornea image data corresponds to a first cornea image data of a patient, whose brain health is being evaluated by method 300, and a second cornea image data, corresponding to a healthy control subject.

Figure 3:
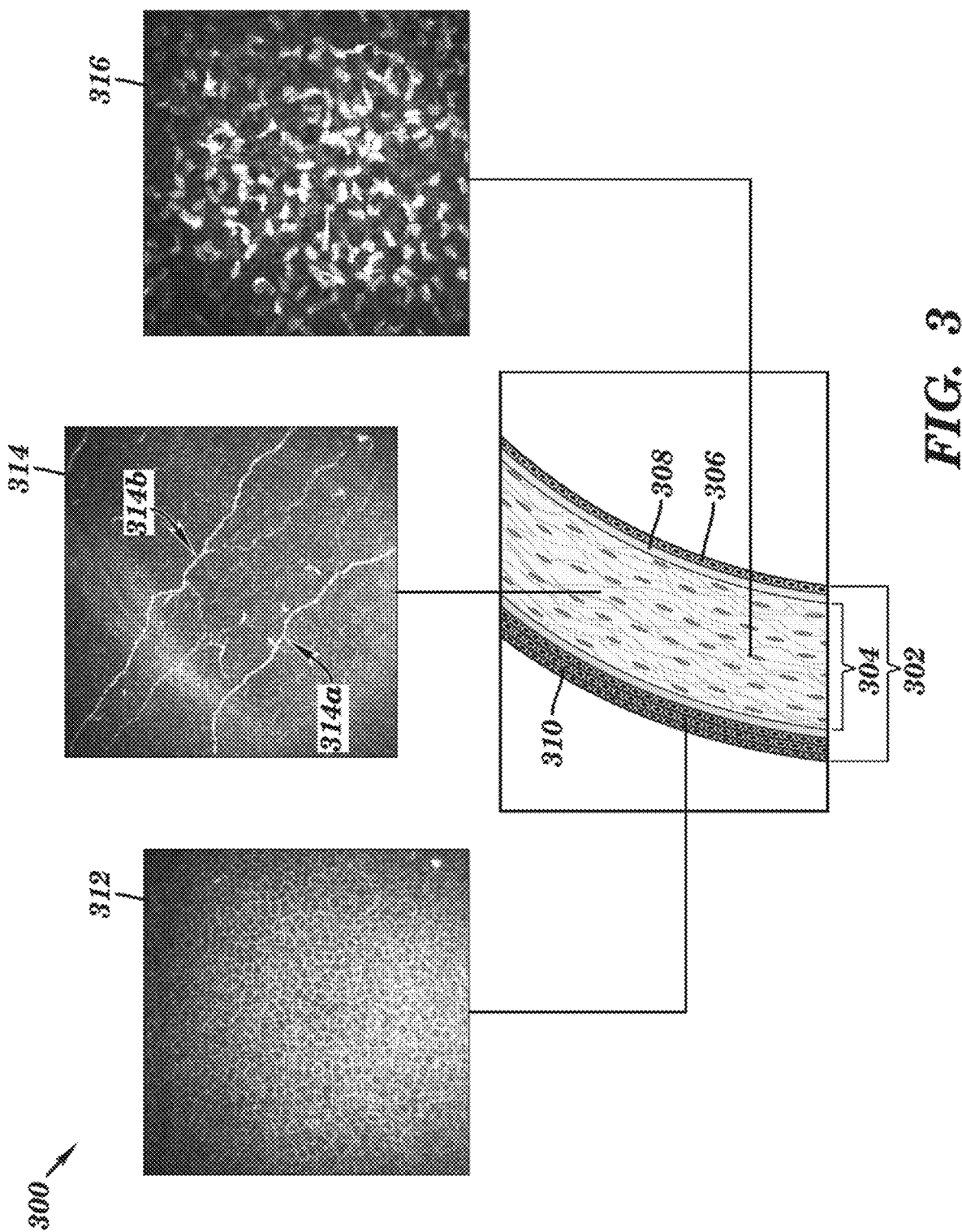
FIG. 3 shows exemplary locations and experimental data for collecting cornea images, according to an embodiment of the present disclosure.

Referring briefly to FIG. 3, a cornea system 300 is shown. The cornea system 300 includes the cornea 302, the stroma 304, the endothelium 306, the Descemet's membrane 308, the epithelium 310. System 300 further includes exemplary image data 312 collected at the epithelium 310, exemplary image data 314 collected at the sub-basal nerve plexus at the interface between the epithelium 310 and the stroma 304, and exemplary image data 316 collected at the stroma 304. In some examples, the received cornea image data of 210 includes image data of the epithelium 310 of a subject and any portion of the stroma 304 of a subject. In some examples, the received cornea image data of 210 includes image data of any portion of the subject's cornea.

Method 200 then provides for determining at least one marker from the received image data 220. Referring again to FIG. 3, healthy image data is shown of a user's cornea. In image 314 of the sub-basal nerve plexus just anterior to the stroma 304, in a healthy subject as shown in FIG. 3, a plurality of corneal nerves (e.g. nerves 314a and 314b) are clearly identifiable. In some examples of the present disclosure, the at least one marker includes a determination of whether the nerves are identifiable in selected portions of the cornea between the epithelium 310 and the stroma 304. For example, the portions of the stroma include specific depth levels.

In some examples, image data 312 is collected at a depth of 0 microns, at the anterior surface of the epithelium. In some examples, image data 314 is collected at a depth of 11 microns. In some examples, image data 316 is collected at a depth of 40 microns.

Figure 4:
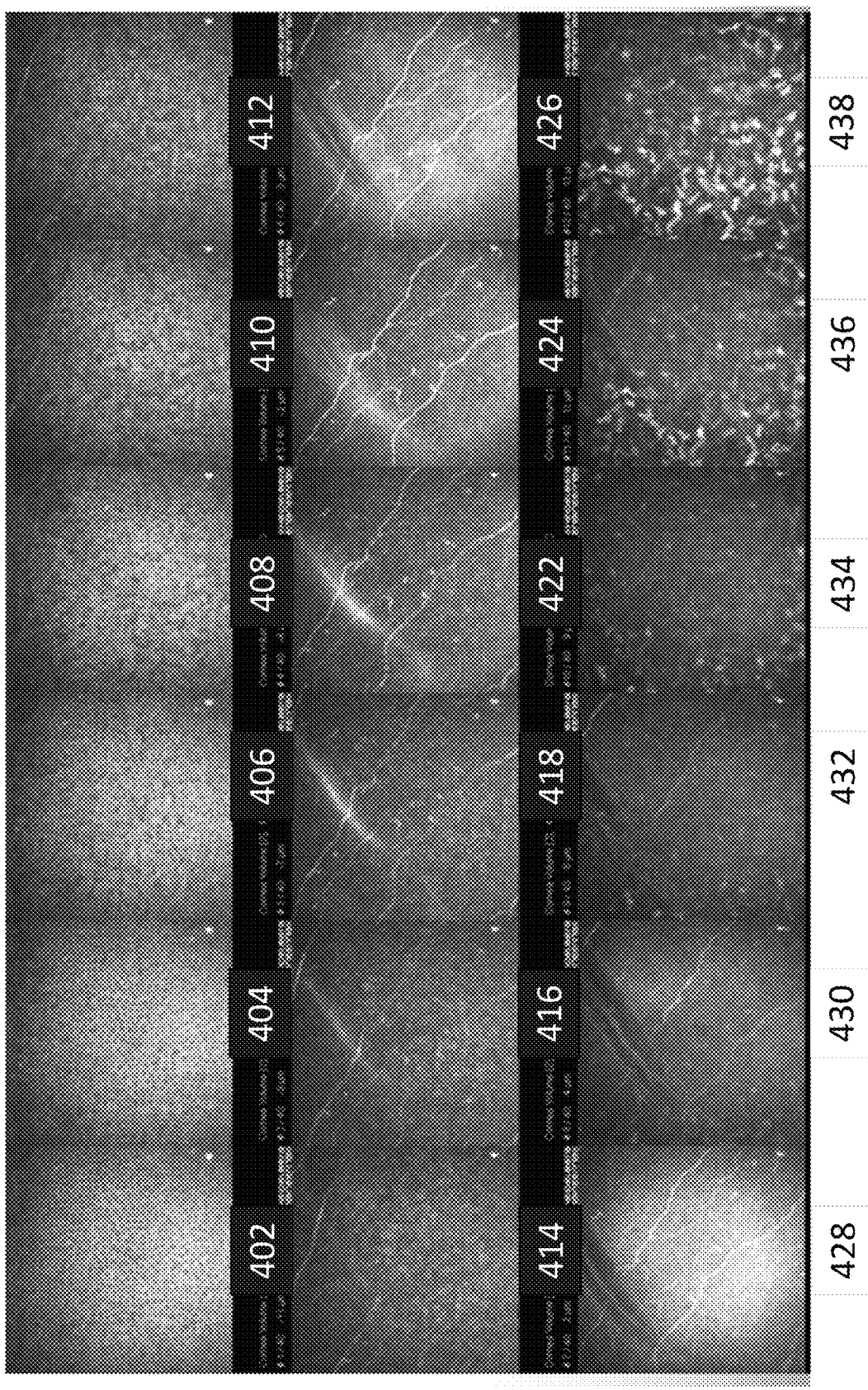
FIG. 4 shows exemplary cornea image data of a healthy subject, according to an embodiment of the present disclosure.
Figure 5:
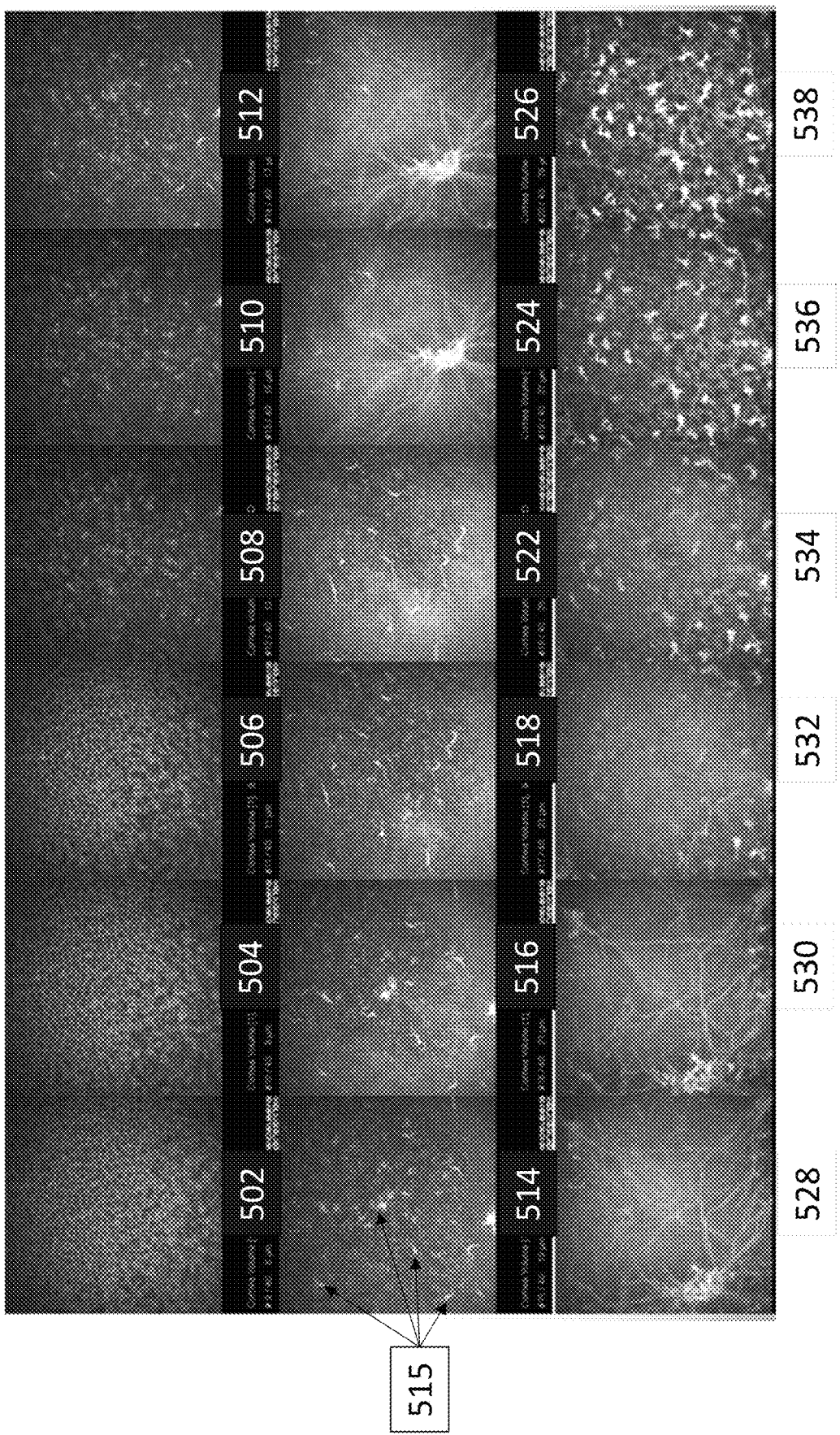
FIG. 5 shows exemplary cornea image data of a subject suffering from migraines, according to an embodiment of the present disclosure.

Turning briefly to FIGS. 4-5, experimental image data is shown at various levels of the cornea for two separate patients. In the image data of a healthy patient (shown in FIG. 4), the nerves are identifiable for a plurality of cornea image data, including for example, images 414-432. In the image data of a patient with a concussion history (shown in FIG. 5), the nerves are less identifiable, missing in some of the images, and interspersed with inflammatory Langerhans cells (e.g., dendritic cells 515 in image 514). The present disclosure contemplates that these dendritic cells migrated from the corneal limbus and indicate brain trauma and/or brain damage. In some examples of 220, the markers include whether these dendritic cells (e.g., fragments 515 in image 514) are visible in the received cornea image data.

In some examples, the marker includes a cornea nerve fiber characteristic, including: a cornea nerve fiber density (CNFD), a cornea nerve branch density (CNBD), a cornea nerve fiber length (CNFL), a cornea nerve fiber total branch density (CTBD), a cornea nerve fiber area (CNFA), a nerve fiber width (CNFW), a nerve fiber orientation histogram, a nerve fiber width histogram, and any combination thereof. In some examples, exemplary ranges of these markers for patients with brain trauma include the following: CNFD: 0-37.5 fibers/mm2; CNBD: 0-56.2 branch points on main fibers/mm2; CNFL: 5.2-18.1 total length of nerves mm/mm2; CTBD 6.2-75.0 total branch points/mm2; CNFA: 0.0035-0.0086 total nerve fiber area mm2/mm2; and CNFW: 0.020-0.26 average nerve fiber width mm/mm2.

In some examples of 220, a plurality of markers is identified in the received cornea image data from 210. One or more of the identified markers are then selected via a machine learning algorithm. For example, the machine learning model is trained on a plurality of sets of cornea image data, which include at least one set of cornea image data corresponding to a healthy subject and at least one set of cornea image data corresponding to a subject with a concussion.

Method 200 then provides for outputting a brain health diagnosis based on the marker 230. In some examples, the brain health diagnosis is based on determining a difference between the at least one marker in the first set of cornea image data and the at least one marker in the second set of cornea image data. For example, the brain health diagnosis includes a concussion severity notification and/or a notification identifying whether a concussion has occurred. In some examples, the brain health diagnosis is output on a display associated with a computing device (e.g., computing device 130 of FIG. 1).

In some examples, a brain health diagnosis is output based on whether a particular marker value is outside of a specified range for that marker. In some examples, a brain health diagnosis is output based on whether a particular marker value is above or below a threshold value for that marker.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Diagnosis and Treatment of a Brain Disease or Brain Injury

The methods and systems provided herein can be used to diagnose, identify, prevent, and/or treat a brain disease or brain injury, which can include but is not limited to a head injury, concussion, or mild traumatic brain injury (mTBI).

A mild traumatic brain injury (mTBI) is a nondegenerative, non-congenital insult to the brain from an external mechanical force that can lead to temporary or permanent cognitive, physical and psychosocial impairment with an associated diminished or altered state of consciousness. TBI can be mild, moderate, or severe. Mild TBI has similar symptoms to that of moderate and severe TBI of inflammation, edema and decreased motor and cognitive functioning. Characteristic, yet not necessarily mutually exclusive, complications of mild TBI include: diffuse axonal injury; and repeated injury, a condition that causes cumulative neurological impairments known as chronic traumatic encephalopathy (CTE).

With multiple head injuries or concussions, such as those endured by athletes, professional drivers, football players, boxers, wrestlers, hockey players, and members of the military, neuropsychological performance decreases over time. These individuals can often suffer from Post-Concussion Syndrome (PCS), the symptoms of which include problems with sleep, memory, attention, and cognition that often last years after injury. With about 25% or approximately 360,000 of the U.S. veterans of Iraq and Afghanistan having sustained mTBI, the likelihood of enduring multiple injuries from improvised explosive device (IED) blast waves is also high. Therefore, identifying mTBI at the earliest stages are crucial for treating and preventing more serious forms of brain disease such as Alzheimer's disease, depression, and Parkinson's disease.

In some examples of the present disclosure, brain health can be assessed using corneal imaging, corneal nerve fiber characteristics, the presence or absence of dry eye, and/or the presence or absence of temperature sensitivity.

Additional examples of the causes, symptoms, and biomarkers for concussions and/or mTBI are known in the art, see e.g., Toledo E, Lebel A, Becerra L, Minster A, Linnman C, Maleki N, Dodick D W, Borsook D. The young brain and concussion: imaging as a biomarker for diagnosis and prognosis. *Neurosci Biobehav Rev.* 2012 July; 36(6):1510-31; Binder, L. M. (1986) Persisting symptoms after mild head injury: a review of the postconcussive syndrome, *J Clin Exp Neuropsychol* 8, 323-346; Lewandowski, L., Rieger, B., Smyth, J., Perry, L., and Gathje, R. (2009) Measuring post-concussion symptoms in adolescents: feasibility of ecological momentary assessment, *Arch Clin Neuropsychol* 24, 791-796; McKee A C, Robinson Me. Military-related traumatic brain injury and neurodegeneration. Alzheimers Dement. 2014; and Meaney, D. F., and Smith, D. H. (2011) Biomechanics of concussion, *Clin Sports Med* 30, 19-31, vii, which are incorporated herein by reference in their entireties.

In some embodiments, provided herein is a method of treating a brain disease (e.g., mTBI). Treatments for brain diseases such as concussion, head injury, and mTBI can include but are not limited to: (1) functional treatments such as cognitive rest, physical rest, removal from physical activity for a period of time, reduced screen time, limiting exposure to bright lights and loud sounds, reduced cognitive concentration, and increased monitoring neurocognitive behavior; (2) pharmacological treatments such as anti-inflammatory agents, non-steroidal anti-inflammatory agents, steroids, anti-depressants, sertraline, amitriptyline, beta (β)-Blockers, calcium channel blockers, valproic acid, topiramate, triptans, dihydroergotamine, gabapentin, methylphenidate, dopaminergic agents, amantadine, melatonin, N-methyl-D-aspartate antagonists, donepezil, rivastigmine, maprotiline, dihydroergotamine, cytidine diphosphoryl choline, fluoxetine, pramiracetam, bromocriptine, atomoxetine; and (3) rehabilitation such as increasing fluids, changing diet, gradually returning to cognitive and physical activities, wear eye protection, increased monitoring of symptoms, etc. Additional examples of treatments can be found, e.g., Meehan WP 3rd. Medical therapies for concussion. Clin Sports Med. 2011; 30(1):115-ix; Chew E, Zafonte RD. Pharmacological management of neurobehavioral disorders following traumatic brain injury—a state-of-the-art review. J Rehabil Res Dev. 2009; 46:851-79; Tenovuo O. Pharmacological enhancement of cognitive and behavioral deficits after traumatic brain injury. Curr Opin Neurol. 2006; 19:528-33; Mittenberg W, Canyock E M, Condit D, et al. Treatment of post-concussion syndrome following mild head injury. J Clin Exp Neuropsychol. 2001; 23:829-36; Reddy CC. A treatment paradigm for sports concussion. Brain Injury Professional. 2004; 4:24-5; amantaray S, Das A, Thakore N P, et al. Therapeutic potential of melatonin in traumatic central nervous system injury. J Pineal Res. 2009; 47:134-42; and Warden D L, Gordon B, McAllister T W, et al. Guidelines for the pharmacologic treatment of neurobehavioral sequelae of traumatic brain injury. J Neurotrauma. 2006; 23:1468-501, each of which is incorporated herein by reference in their entireties.

EXAMPLES

Example 1: Experimental Data

Figure 6:
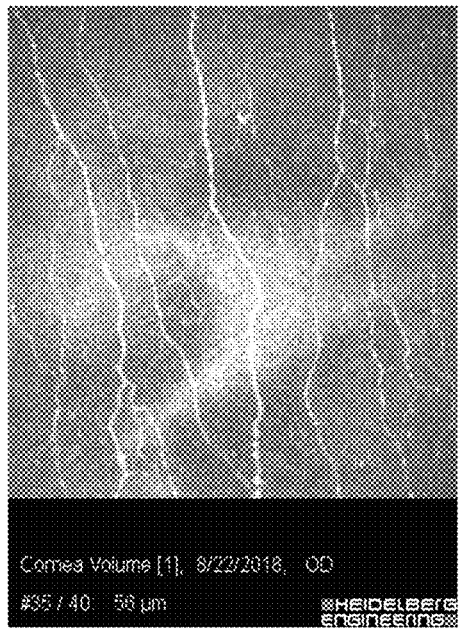
FIG. 6 shows exemplary cornea image data compared between four subjects, according to an embodiment of the present disclosure.
Figure 6:
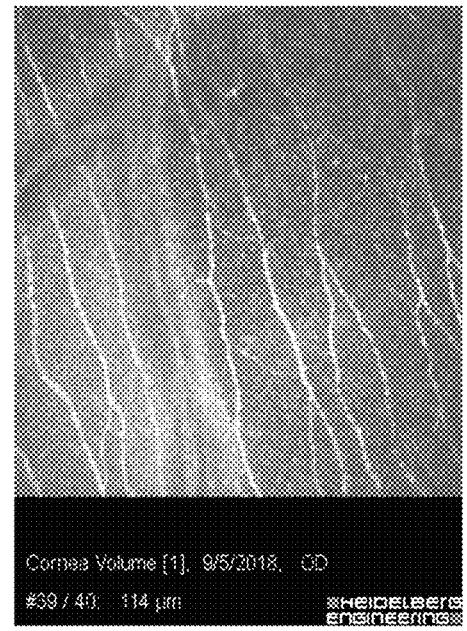
Figure 6:
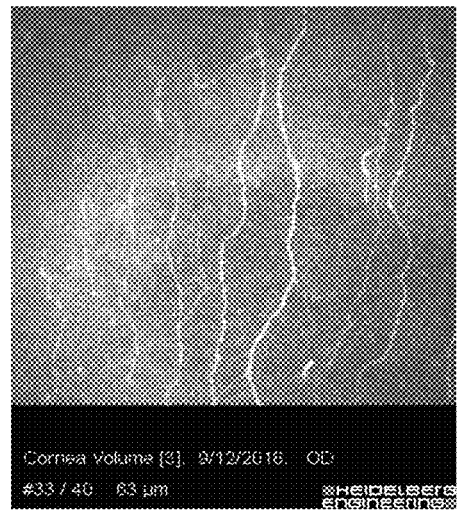
Figure 6:
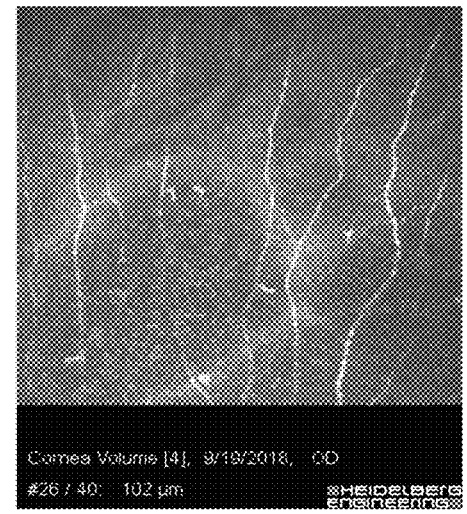

FIG. 6 shows exemplary cornea image data compared between four subjects, according to an embodiment of the present disclosure. Image 610 shows cornea image data of a subject with episodic migraines. Methods according to the present disclosure provide for identifying various markers in image 610, including CNFD at 31.2; CNBD at 56.2; CNFL at 17.6; CTBD at 68.7; CNFA at 0.006; and CNFW at 0.02. Image 620 shows cornea image data of a subject with chronic migraines. Methods according to the present disclosure provide for identifying various markers in image 620, including CNFD at 75.0; CNBD at 37.5; CNFL at 20.3; CTBD at 37.5; CNFA at 0.006; and CNFW at 0.02. For example, the levels of CNFD are greatly elevated and the levels of CNBD and CTBD are greatly reduced in a patient with chronic migraines (image 620) as compared to a patient with infrequent migraines (image 610).

Image 630 shows cornea image data of a subject with daily persistent headaches at a depth of 63 micrometers. Methods according to the present disclosure provide for identifying various markers in image 630, including CNFD at 25.0; CNBD at 6.2; CNFL at 15.0; CTBD at 31.2; CNFA at 0.004; and CNFW at 0.02. Image 640 shows cornea image data of a subject with chronic daily, tension-type headaches at a depth of 102 micrometers. Methods according to the present disclosure provide for identifying various markers in image 640, including CNFD at 25.0; CNBD at 12.5; CNFL at 12.9; CTBD at 18.7; CNFA at 0.004; and CNFW at 0.02. For example, the levels of CTBD are elevated and the levels of CNBD are reduced in a patient with daily persistent headaches (image 630) as compared to a patient with chronic daily, tension-type headaches (image 640). Image 630 also shows some Langerhans cells (6 flecks) indicating the presence of inflammation.

Figure 7:
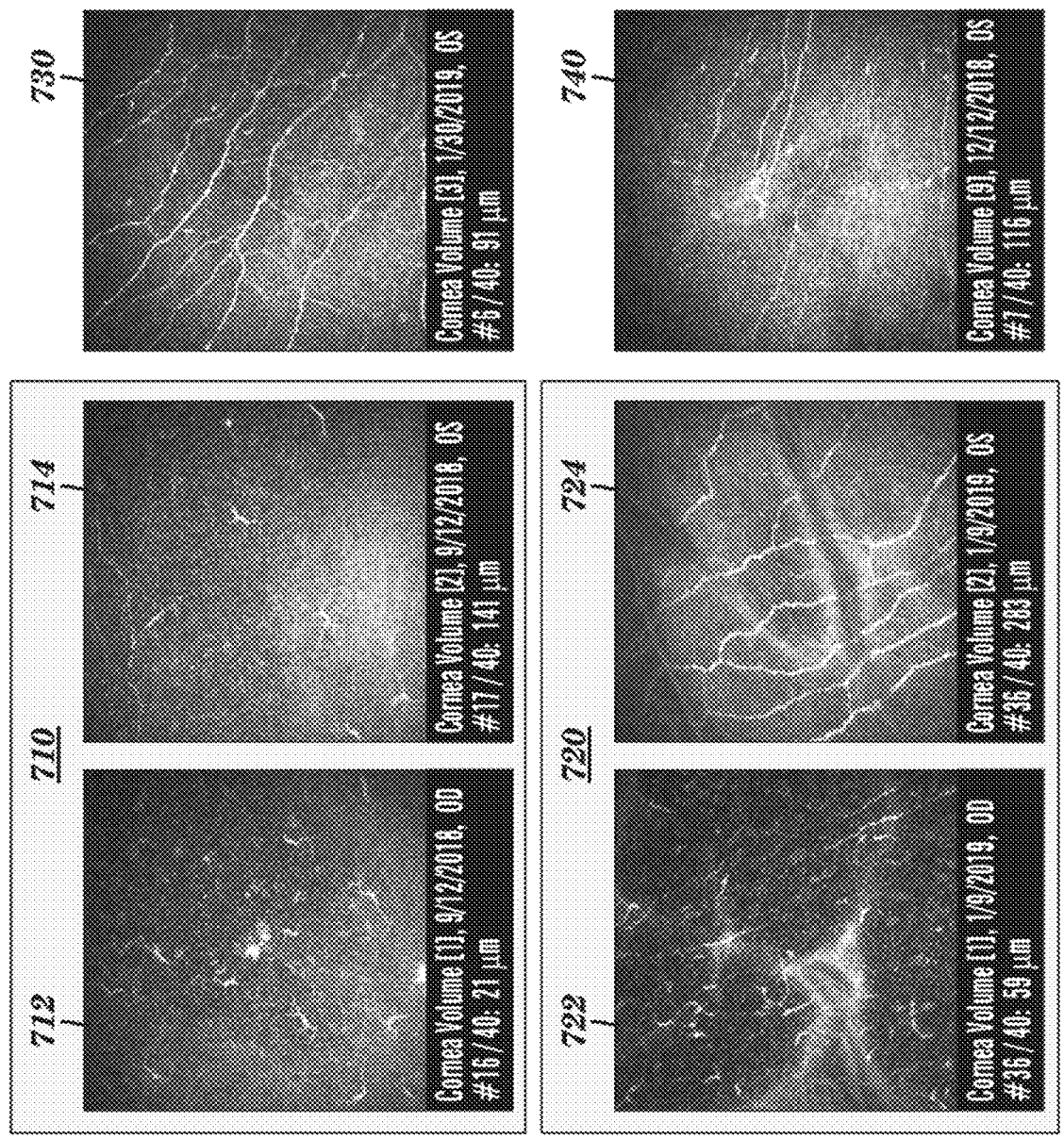
FIG. 7 shows exemplary cornea image data compared between four subjects with prior concussive history, according to an embodiment of the present disclosure.

FIG. 7 shows exemplary cornea image data compared between four subjects with prior concussive history and a history of post-traumatic headaches, according to an embodiment of the present disclosure. Image set 710 shows a right eye image 712 and a left eye image 714. The present disclosure provides for determining that image set 710 corresponds to a patient with high brain trauma due to the lack of visible cornea nerves and the presence of Langerhans cells. Image set 720 shows a right eye image 722 and a left eye image 724. The present disclosure provides for determining that image set 720 corresponds to a patient with high brain trauma due to the lack of clear cornea nerves and the extensive Langerhans cells in the right eye 722. Image 730 shows a left eye image with Langerhans cells. Image 740 shows a left eye image also with Langerhans cells.

Therefore, the exemplary experimental data, as shown in FIGS. 6 and 7, provides a non-invasive approach, which is easily repeated for the same region. Therefore, the detected changes in nerve metrics can provide a measure of various pain conditions, both peripheral and central. The morphology of the radial penetrating nerves of the cornea provide more information on nerve morphometry than skin biopsies; this additional information includes fiber density, fiber length and fiber branching, and other elements that cannot be obtained with skin biopsies.

Figure 8:
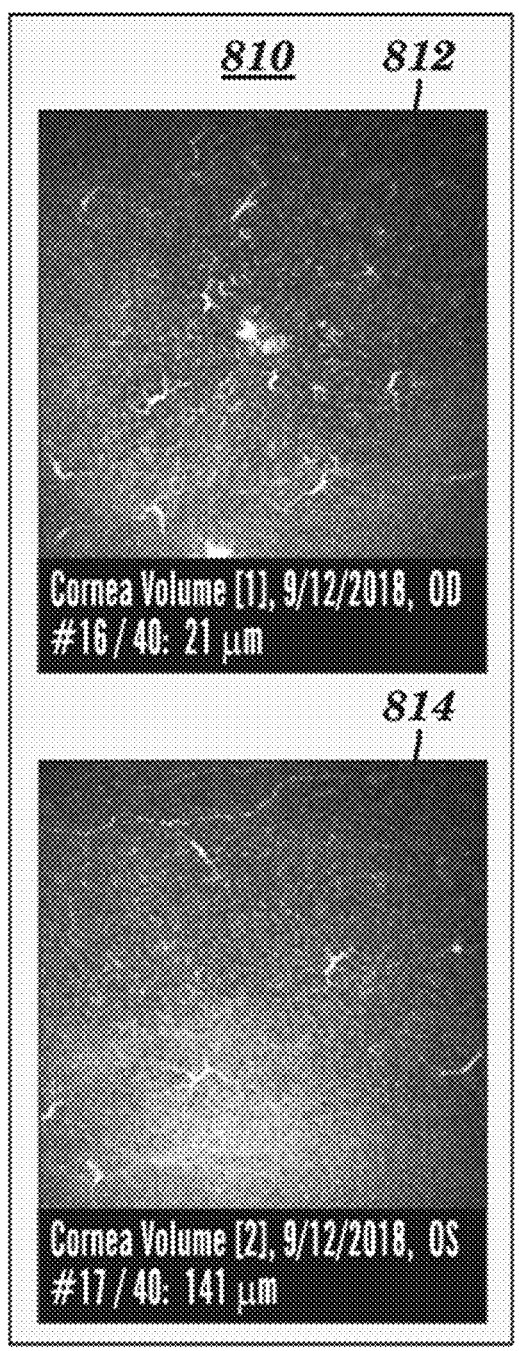
FIG. 8 shows exemplary cornea image data over time for a subject, according to an embodiment of the present disclosure.
Figure 8:
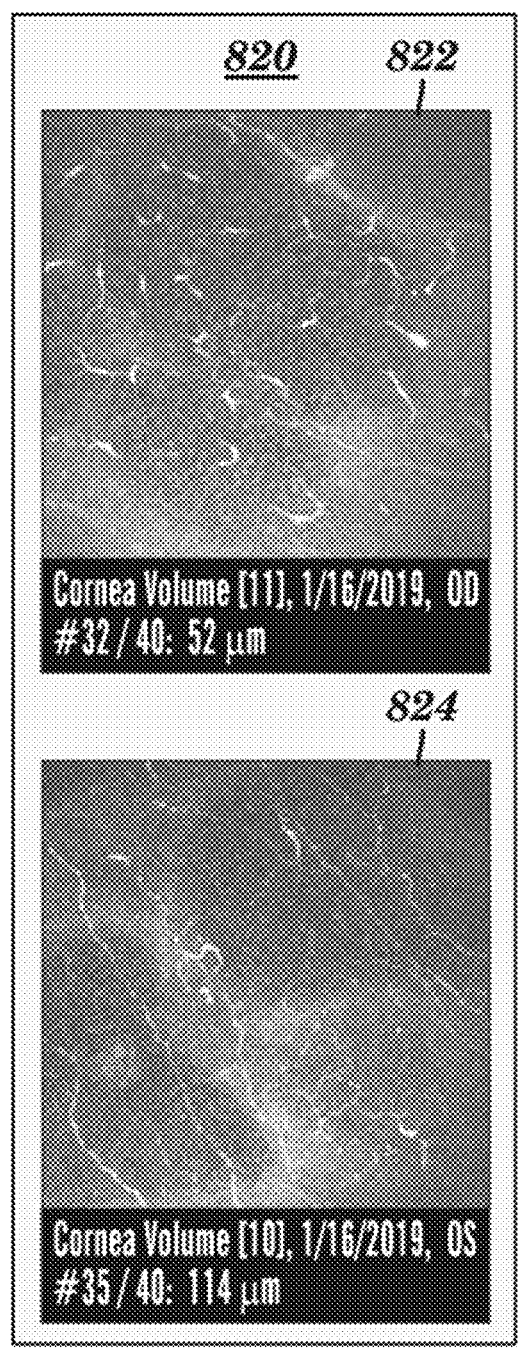

FIG. 8 shows exemplary cornea image data over time for a subject, according to an embodiment of the present disclosure. Image set 810 shows a right eye image 812 and a left eye image 814 collected at a first time period. Image set 820 shows a right eye image 812 and a left eye image 814. Image set 820 was collected four months later than image set 810. Image set 820 demonstrates that the patient is slowly recovering, as cornea nerves are more visible in the image set 820 than in the image set 810. Additionally, the Langerhans cells are smaller in the image set 820 than in the image set 810.

Example 2: Altered Corneal Fiber Length in Patients with mTBI

Purpose:

Cornea innervation provides a window into changes in peripheral nerves within the ophthalmic division of the trigeminal system. Mild traumatic brain injury (mTBI) has been suggested to be comorbid with dry eye, suggesting an underlying corneal afferent pathology. Corneal pathology may underlie the start of dry eye in mTBI. We examined a cohort of mTBI patients to establish whether corneal nerve changes are present and if so, can be quantified with in vivo corneal microscopy (IVCM).

Methods:

IVCM was performed in a preliminary cohort of 18 patients (9 females, 9 males, average age 24.7 yrs [13-63 yrs]) with a diagnosis of mTBI (average time from recent diagnosis: 1.9 yrs [3 days-14 years]). Patients were recruited from the Pediatric Headache Clinic at Boston Children's Hospital and the Cantu Concussion Clinic at Emerson Hospital. Images were acquired using a Heidelberg Retina Tomograph 3 with a Rostock Corneal Module, and the fully automated software package ACCmetrics (Manchester, UK) quantitated corneal nerve morphology metrics including nerve fiber density (NFD), nerve branch density (NBD), and nerve fiber length (NFL). Identification of corneal nerve pathology was determined by comparison between mTBI patients and published normative values of categorical age-matched healthy controls (Tavakoli et al., Diabetes Care 2015). Surveys were administered to record the presence or absence of ocular surface disease (Ocular Surface Disease Index), ocular pain (Ocular Pain Assessment Survey), and the symptoms and severity of concussion (Post-Concussive Symptom Score).

Results:

NFL was systematically lower in mTBI patients vs. the bottom 5%-quantile of normative values in nearly every sex-age category: females under 16 (n=1), 16-25 (n=4), 36-45 (n=2), and 46-55 years old (n=1), and males under 16 (n=3), and 16-25 years old (n=6). Females 56-65 (n=1) with mTBI did not fall below the 5%-quantile normative cutoff. NFD and NBD were lower in mTBI patients vs. normative values in both male (n=3) and female groups (n=1) under 16 years old only.

Conclusions:

Corneal afferent abnormalities can be detected in mTBI patients, and corneal afferents may be particularly susceptible to disruption in patients under the age of 16. The consistent decreases across age suggest a common pathophysiology separate from age-related processes. It is contemplated herein that shear injury and/or inflammatory processes contribute to the altered corneal nerve fiber length.

Figure 9:
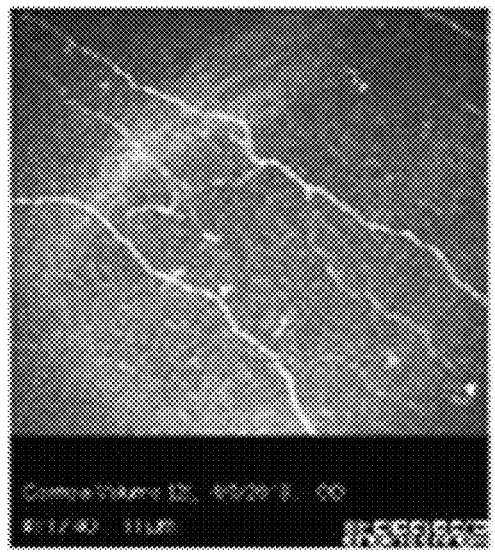
FIG. 9 shows exemplary cornea image data demonstrating decreased corneal nerve fiber integrity in three concussion patients (bottom) relative to a healthy control subject (top). Each image represents a 400×400 micron area at the corneal apex at the level of the sub-basal nerve plexus, between the corneal epithelium and the stroma. The healthy control patient showed clear, distinct corneal innervation at this depth. The mTBI patients show desiccated corneal nerves and increased presence of Langerhans cells (speckled hyperintensities), which are associated with corneal inflammation. Images were collected using a Heidelberg Retina Tomograph III with a Rostock Cornea Module.
Figure 9:
Figure 9:
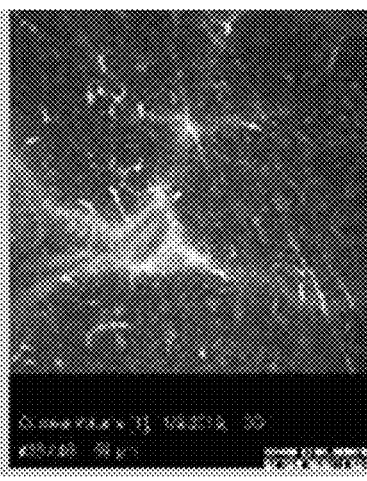
Figure 9:

Example 3: Using Corneal Microscopy to Quantify Morphological Features of Corneal Afferents in Pediatric Concussion Patients Micron-resolution optical images of corneal afferents from 14 patients (17.4±3.4 years old, 9 males, 5 females) with a history of concussion were collected. The images are striking, with several patients showing visible degeneration of these afferents compared to what is observed in a healthy individual (FIG. 9). The quantitative measures of afferent morphology better represent the distribution of measures across individual patients, and were assessed with ACCmetrics. 52-54 Our preliminary data indicate that young patients with concussion, and especially in children, have a decrease in corneal nerve fiber density, nerve branching, and nerve fiber length from compared to age-matched controls (data not shown). This experimental data suggests that peripheral damage of trigeminal nerve branches may occur following concussion.

Figure 10:
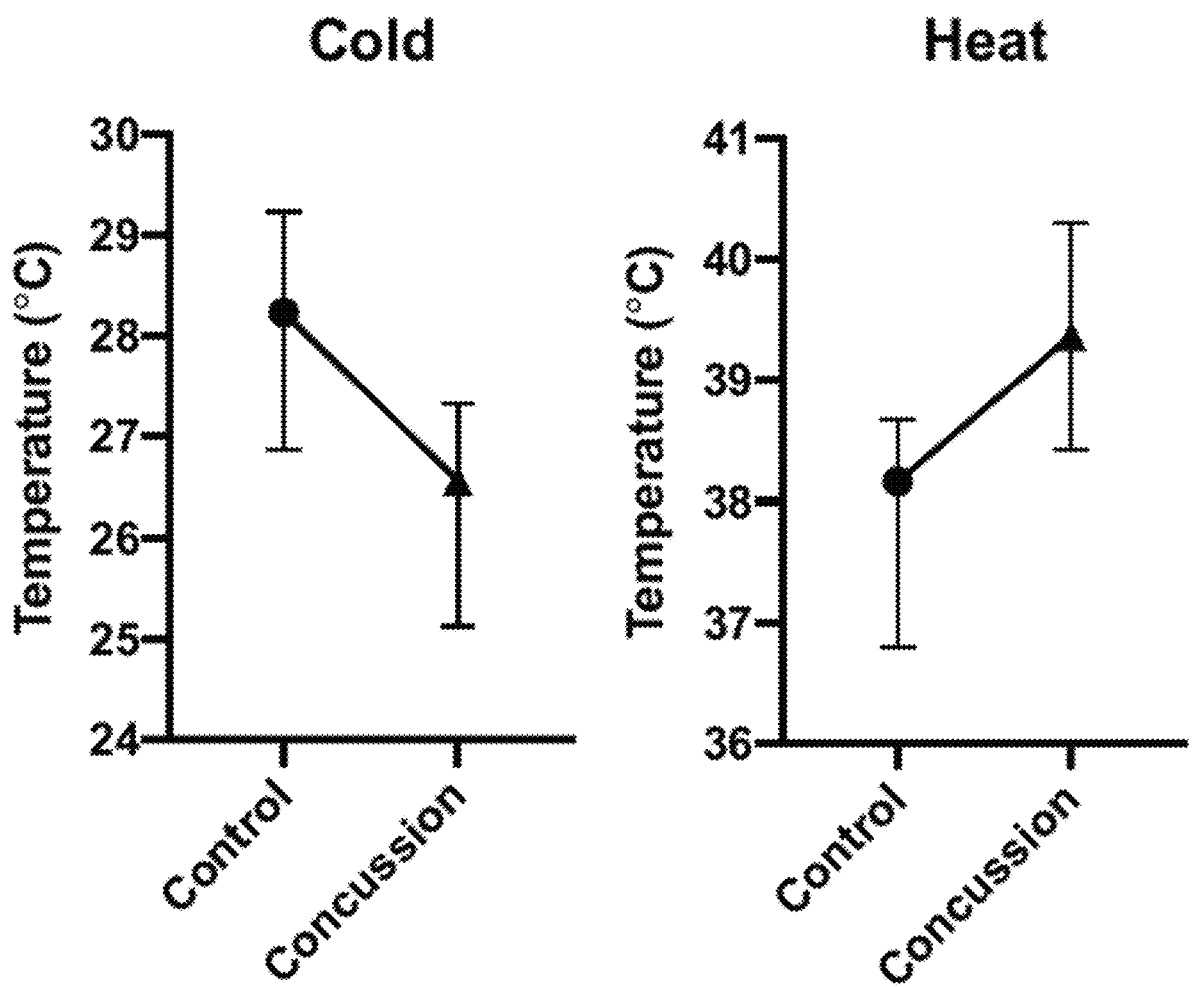
FIG. 10 shows bar graphs illustrating pain detection thresholds for patients with concussions.

It was discovered that concussion patients have decreased thermal pain thresholds when tested within the ophthalmic representation of the trigeminal sensory dermatome. In a cohort of 17 healthy controls and 15 individuals (age range: 10-21 years) with a recent mTBI who had a post-traumatic headache, thermal pain sensitivity was examined using quantitative sensory testing (FIG. 10). A 30×30 mm contact thermode was applied to the right temple (innervated by the ophthalmic division of the trigeminal nerve). A series of three hot and cold temperature sensitivity challenges were performed where participants were asked to identify when they experienced a temperature as painful. As shown in FIG. 10, participants who had an mTBI required a greater change from baseline in both the cold and hot temperature trials to identify the stimulus as being painful. These findings show an atypical neurophysiological performance of nociceptors connected with the trigeminal nerve.

Accordingly, because the trigeminal nerve the same nerve that innervates the cornea. There may be a relationship between corneal nerve health (an indicator of trigeminal nerve health) and pain detection thresholds (another indicator of trigeminal nerve health), and in some examples, the pain detection thresholds may be input into machine learning or other algorithms to output a health status.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system for diagnosing brain health, comprising:
   a microscope configured to output image data of a cornea of a patient;
   a processor; and
   a memory having stored therein a plurality of code sections executable by the processor, the plurality of code comprising instructions for:
   receiving cornea image data from the microscope;
   determining at least one marker from the received cornea image data, wherein said determining comprises:
   identifying a plurality of markers in the received cornea image data; and
   selecting, via a machine learning algorithm, one or more of the identified markers; and
   outputting a brain health diagnosis based on the at least one marker.

2. The system of claim 1, wherein each of the at least one marker comprises a cornea nerve fiber characteristic.

3. The system of claim 2, wherein the cornea nerve fiber characteristic comprises at least one of: a nerve fiber density, a nerve branch density, a nerve fiber length, a nerve fiber total branch density, a nerve fiber area, a nerve fiber width, a nerve fiber orientation histogram, and a nerve fiber width histogram.

4. The system of claim 1, wherein receiving cornea image data further comprises:
   receiving a first set of cornea image data; and
   receiving a second set of cornea image data.

5. The system of claim 4, wherein the brain health diagnosis is based on determining a difference between the at least one marker in the first set of cornea image data and the at least one marker in the second set of cornea image data.

6. The system of claim 4, wherein the first set of cornea image data corresponds to a left eye of a patient and the second set of cornea image data corresponds to a right eye of a patient.

7. The system of claim 4, wherein the first set of cornea image data corresponds to image data at a first time, and the second set of cornea image data corresponds to image data at a second time, wherein the first time is earlier than the second time.

8. The system of claim 1, wherein the brain health diagnosis comprises at least one of: a concussion severity notification and a notification identifying whether a concussion has occurred.

9. The system of claim 1, wherein the machine learning model is trained on a plurality of sets of cornea image data comprising at least one set of cornea image data corresponding to a healthy subject and at least one set of cornea image data corresponding to a subject with a concussion.

10. A method, comprising:
receiving cornea image data from a microscope;
determining at least one marker from the received cornea image data, wherein said determining comprises:
identifying a plurality of markers in the received cornea image data; and
selecting, via a machine learning algorithm, one or more of the identified markers; and
outputting a brain health diagnosis based on the at least one marker.

11. The method of claim 10, wherein each of the at least one marker comprises at least one of: a nerve fiber density, a nerve branch density, a nerve fiber length, a nerve fiber total branch density, a nerve fiber area, a nerve fiber width, a nerve fiber orientation histogram, and a nerve fiber width histogram.

12. The method of claim 10, wherein receiving cornea image data further comprises:
receiving a first set of cornea image data; and
receiving a second set of cornea image data.

13. The method of claim 10, wherein the brain health diagnosis comprises at least one of: a concussion severity notification and a notification identifying whether a concussion has occurred.

14. A non-transitory machine-readable medium comprising machine-executable code, which, when executed by at least one machine, causes the machine to:
receive cornea image data from a microscope;
determine at least one marker from the received cornea image data, wherein said determining comprises:
identifying a plurality of markers in the received cornea image data; and
selecting, via a machine learning algorithm, one or more of the identified markers; and
output a brain health diagnosis based on the at least one marker.

15. The non-transitory machine-readable medium of claim 14, wherein each of the at least one marker comprises at least one of: a nerve fiber density, a nerve branch density, a nerve fiber length, a nerve fiber total branch density, a nerve fiber area, a nerve fiber width, a nerve fiber orientation histogram, and a nerve fiber width histogram.

16. The non-transitory machine-readable medium of claim 14, wherein receiving cornea image data further comprises:
receive a first set of cornea image data; and
receive a second set of cornea image data.

17. The non-transitory machine-readable medium of claim 14, wherein the brain health diagnosis comprises at least one of: a concussion severity notification and a notification identifying whether a concussion has occurred.

18. The non-transitory machine-readable medium of claim 14, wherein the machine-executable code, which, when executed by at least one machine, further causes the machine to receive a set of thermal pain threshold detection data and wherein based on the at least one marker further comprises the set of thermal pain threshold detection data.

19. The non-transitory machine-readable medium of claim 18, wherein the set of thermal pain threshold detection data is received post application of a thermal stimulus to the right temple of a patient.

20. The non-transitory machine-readable medium of claim 19, wherein the thermal stimulus is an increasing or decreasing temperature of an object applied to the right temple.

* * * * *